United States Patent

Lavene

[19]

[11] Patent Number: 6,111,743
[45] Date of Patent: Aug. 29, 2000

[54] METALLIZED CAPACITOR HAVING INCREASED DIELECTRIC BREAKDOWN VOLTAGE AND METHOD FOR MAKING THE SAME

[75] Inventor: Bernard Lavene, Ocean, N.J.

[73] Assignee: Electronic Concepts, Inc., Eatontown, N.J.

[21] Appl. No.: 09/239,853

[22] Filed: Jan. 29, 1999

Related U.S. Application Data

[63] Continuation-in-part of application No. 08/806,849, Feb. 26, 1997, abandoned, which is a continuation of application No. 08/282,308, Jul. 29, 1994, Pat. No. 5,614,111, which is a continuation-in-part of application No. 08/198,846, Feb. 18, 1994, Pat. No. 5,610,796, which is a continuation-in-part of application No. 08/127,867, Sep. 28, 1993, Pat. No. 5,608,600, which is a continuation-in-part of application No. 08/020,344, Feb. 19, 1993, abandoned.

[51] Int. Cl.⁷ .................... H01G 4/005; H01G 4/32; H01G 7/00
[52] U.S. Cl. .................. 361/301.5; 361/303; 361/273; 29/25.42
[58] Field of Search ............. 361/301.5, 303, 361/304–305, 309, 323, 273; 29/29.42

[56] References Cited

U.S. PATENT DOCUMENTS

| | | | |
|---|---|---|---|
| 3,185,907 | 5/1965 | McKee et al. | 361/305 |
| 3,457,478 | 7/1969 | Lehrer | 361/304 |
| 3,585,468 | 6/1971 | Chertok | 361/301.5 |
| 3,602,770 | 8/1971 | McMahon | 361/11 |
| 3,628,108 | 12/1971 | Craig | 361/304 |
| 3,644,805 | 2/1972 | Heywang | 361/273 |
| 4,072,976 | 2/1978 | Harari | 361/273 |
| 4,306,274 | 12/1981 | Yamagiwa et al. | 361/304 |
| 4,320,437 | 3/1982 | Shaw et al. | 361/305 |
| 4,470,097 | 9/1984 | Lavene | 361/304 |
| 4,477,858 | 10/1984 | Steiner | 361/273 |
| 4,642,731 | 2/1987 | Shedigan | 361/319 |
| 4,685,026 | 8/1987 | Lavene | 29/25.42 |
| 4,719,539 | 1/1988 | Lavene | 361/307 |
| 4,926,862 | 5/1990 | Miyajima et al. | 428/419 |
| 5,262,920 | 11/1993 | Sakuma et al. | 361/305 |

FOREIGN PATENT DOCUMENTS

| | | |
|---|---|---|
| 607826 | 11/1960 | Canada . |
| 44710 | 2/1990 | Japan . |
| 311017 | 11/1992 | Japan . |

OTHER PUBLICATIONS

Hiromasa Matsui et al., "Metalized Film Capacitors with High Energy Density for Rail Vehicles", IEEE, 1997, 15 pages.

*Primary Examiner*—Dean A. Reichard
*Assistant Examiner*—Anthony Dinkins
*Attorney, Agent, or Firm*—Ratner & Prestia

[57] ABSTRACT

A metallized wound capacitor which includes first and second dielectric webs. A first electrode having first and second portions is metallized on the first face of the first web. A second electrode having first and second portions is metallized on the first face of the second web. Either the first electrode, the second electrode, or both, are included of a plurality of spaced apart segments interconnected by wirings. The first and second electrodes extend from opposing dielectric web longitudinal edges leaving respective bare margins along opposing edges on the respective webs. Each second portion has a width equal to the opposing bare margin less a predetermined tolerance and is thicker than its respective first portion.

21 Claims, 4 Drawing Sheets

METALLIZED CAPACITOR HAVING INCREASED DIELECTRIC BREAKDOWN VOLTAGE AND METHOD FOR MAKING THE SAME

This application is a continuation-in-part application of U.S. patent application Ser. No. 08/806,849 filed Feb. 26, 1997 now abandoned, which is a continuation application of U.S. patent application Ser. No. 08/282,308 filed Jul. 29, 1994 now U.S. Pat. No. 5,614,111, which is a continuation-in-part application of U.S. patent application Ser. No. 08/198,846 filed Feb. 18, 1994 now U.S. Pat. No. 5,610,796, which is a continuation-in-part application of U.S. patent application Ser. No. 08/127,867 filed Sep. 28, 1993 now U.S. Pat. No. 5,608,600, which is a continuation-in-part of U.S. patent application Ser. No. 08/020,344 filed Feb. 19, 1993 now abandoned.

FIELD OF THE INVENTION

The invention relates generally to a metallized film capacitor and more particularly to producing a metallized film capacitor with increased dielectric breakdown voltage.

BACKGROUND OF THE INVENTION

A standard metallized film capacitor widely known in the art is the wound capacitor. Wound capacitors are constructed by sandwiching a dielectric film such as polycarbonate, polypropylene or polyester film between metal electrodes (e.g., vapor deposited metal film). Once formed, the combination dielectric/metal material is wound to form a capacitor. Some specific examples of wound capacitors are found in the following: U.S. Pat. No. 4,320,437 (Shaw et al.), U.S. Pat. No. 4,719,539 (Lavene), and U.S. Pat. No. 4,685,026 (Lavene).

In making wound capacitors and particularly pulse and AC wound capacitors, a problem has been in forming the lead termination. The ends of the wound capacitor have been sprayed with molten metal particles to form terminals engaging the electrodes metallized on the dielectric web. Leads have been bonded to the terminals. In order to decrease the ESR (equivalent series resistance), decrease the dissipation factor and increase the reliability of the connection between the metallization and the spray, it has been crucial to have a substantial amount of metallization defined at the capacitor end, since it is such metallization which is in electrical connection with the metal spray. The art has sought a high quality connection with as low resistance as possible. This is particularly important with thin film dielectrics and low voltage capacitors requiring low losses and low ESR.

In order to assure at least one thickness of metallization at each capacitor end the dielectric webs have been offset one from the other. This has been particularly important in view of material distortion or irregularity and travel of one dielectric web with respect to the other as a result of irregularities in the winding process caused, for example, by machine wear. The dielectric webs have been offset so that each metallized edge extends outwardly. Accordingly, even if the winding machine causes a major amount of irregularity there would still be an exposed edge of metallization at the capacitor end. However, such offset is objectionable when making small sized wound capacitors, since it substantially decreases the volumetric efficiency of the capacitor. A conventional offset can increase the size of such capacitors by approximately 20%.

Also related to the size of the capacitor is the breakdown voltage. The size of a metallized film capacitor is substantially dictated by the thickness of its dielectric film. The thickness of the dielectric, in turn, is dictated by the required overall breakdown voltage of the capacitor. For instance, if a manufacturer cites a particular film as having a dielectric strength of 200 volts $\mu$ and the capacitor design calls for a dielectric breakdown voltage of 400 volts, then the film may be 2 $\mu$ thick.

The maximum electrostatic energy that can be stored in a metallized film capacitor depends on the total capacitance of the capacitor and the square of the maximum voltage that can be safely applied across the capacitor (its breakdown voltage). The breakdown voltage of a capacitor depends on the dielectric strength and the thickness of the film.

Electrolytic capacitors have been commonly used as energy storage devices because they can be made small with high energy storage capability. However, electrolytic capacitors have many drawbacks. The drawbacks include: (1) a high dissipation factor, (2) capacitance decreases with increasing frequency, (3) capacitance substantially decreases with decreasing temperature, (4) because electrolytic capacitors are very lossy, they produce only about 80% efficiency on discharges, (5) electrolytic capacitors tend to leak and (6) if electrolytic capacitors remain idle for an extended period of time, the oxide on the aluminum must be reformed which requires precious battery power.

An additional important requirement of capacitors is for high current applications such as in switching power supplies and filters. To allow the capacitor to handle high currents, the thickness of the metallized layer has been increased. However, the thick metallized layer has been damaged by a short in the dielectric unless the voltage has been unacceptably reduced.

SUMMARY OF THE INVENTION

A metallized wound capacitor includes first and second dielectric webs each having a first face, a second face and a width. A first electrode having first and second portions is metallized on the first face of the first web, to a width less than the width of the first web. A second electrode having first and second portions is metallized on the first face of the second web. The first electrode, the second electrode, or both are comprised of multiple segments interconnected by wirings. The first and second electrodes extend from opposing dielectric web longitudinal edges leaving respective bare margins along opposing edges on the respective webs. The second portion of the first electrode opposes the bare margin on the second web and the second portion of the second electrode opposes the bare margin on the first web. The dielectric webs are then arranged in a capacitor roll with the first and second electrodes in superposed relation to each other.

DETAILED DESCRIPTION OF THE INVENTION

A metallized film capacitor similar to the present invention is found in U.S. Pat. No. 4,420,097 issued to Lavene on Sep. 4, 1984 which is herein incorporated by reference. Also, herein incorporated by reference are U.S. patent application Ser. Nos. 08/020344 and 08/806,849 now abandoned.

The present invention involves varying the metallization thickness on a metallized film capacitor in order to effectively vary the dielectric strength of the dielectric film.

Figure 1:
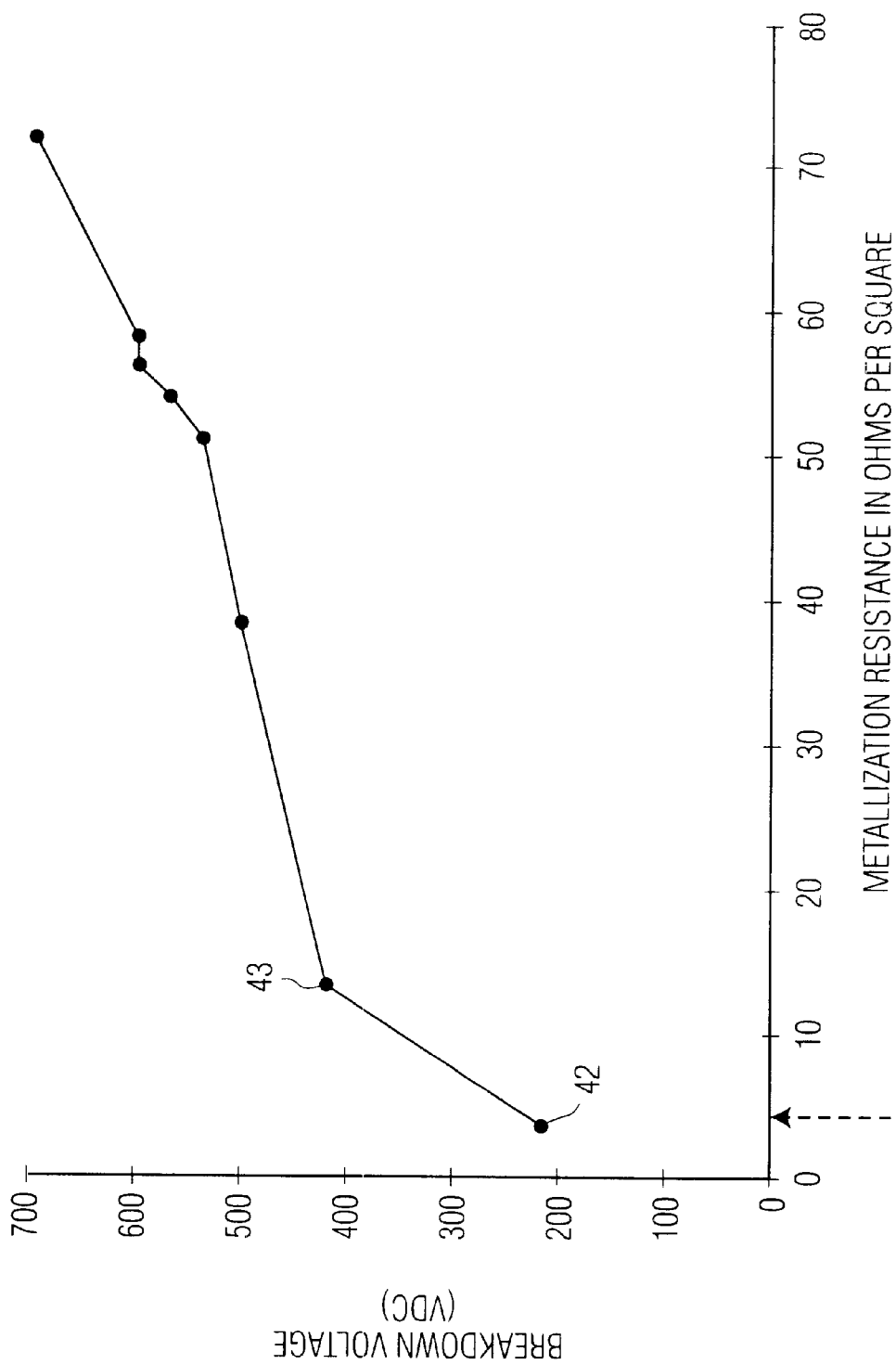
FIG. 1 is a graph illustrating the relationship between metallization thickness and dielectric breakdown voltage.

FIG. 1 is a graph illustrating the relationship between metallization thickness and dielectric breakdown voltage. The graph shows, for example, that increasing the metallization resistance by 3–4 times (from 4 ohms/square at point 42 to 14 ohms/square at point 43) the breakdown voltage is increased by approximately 2 times (from 210 volts/$\mu$ to 420 volts/$\mu$). It should be noted that reducing the metallization thickness increases the metallization resistance through differing slopes.

The ability to vary the dielectric strength of a dielectric film without increasing its thickness translates into smaller metallized film capacitors with higher dielectric breakdown voltages. The practical consequence of this is potentially quite broad.

Metallized film capacitors employing the present invention can match, and even better, the small size of electrolytic capacitors. For example, to match the size of a comparable electrolytic capacitor, the dielectric strength of a given film would have to increase from approximately 200 volts/$\mu$ to approximately 300 volts/$\mu$. By reducing the metallization thickness in accordance with the present invention, the dielectric strength of the film can be increased from 200 volts/$\mu$ to approximately 700 volts/$\mu$.

In the capacitor industry, standard metallization thicknesses vary from 1–4 ohms/sq. The exemplary embodiment of the present invention makes the metallization as thin as possible without losing the capacitor (i.e. there is no metal, hence, no electrode). In addition, the metallization should be as thin as possible while retaining the ability to handle various levels of ripple current, as for example approximately 3%–5%. Currently, metallization thicknesses within the range of 5–300 ohms/square have been achieved. By varying the metallization thicknesses, the dielectric strengths of some films cited by manufacturers have been effectively increased by as much as 250%.

One example of this is a dielectric known as PEN manufactured by DuPont. DuPont's accompanying product literature indicates that PEN has a dielectric strength of approximately 230 volts/$\mu$. By reducing the thickness of the metallization to between 40–70 ohms/square, the effective dielectric strength was increased to approximately 530 volts/$\mu$.

The effectively increased dielectric strength allows for the production of smaller capacitors with higher dielectric strengths which are needed, for example, in devices such as implantable defibrillators.

Additionally, it should be noted that ideal dielectric strengths or intrinsic voltage values (determined in laboratory tests using polished electrodes and oil by manufacturers such as DuPont) for polyester films which range from approximately 15,000–20,000 volts/mil are difficult, if not impossible, to achieve this ideal in practice (i.e., in a commercially made capacitor). The dielectric strengths achieved in practice are generally about ¼ of the ideal; however, by making the metallization thickness as thin as possible, dielectric strengths in practice may be made greater than ½ of the ideal or approximately 12,000 volts/mil.

The exemplary embodiment of the present invention uses many of the construction techniques found in U.S. Pat. 4,470,097 (Lavene) which is herein incorporated by reference.

Figure 2A:
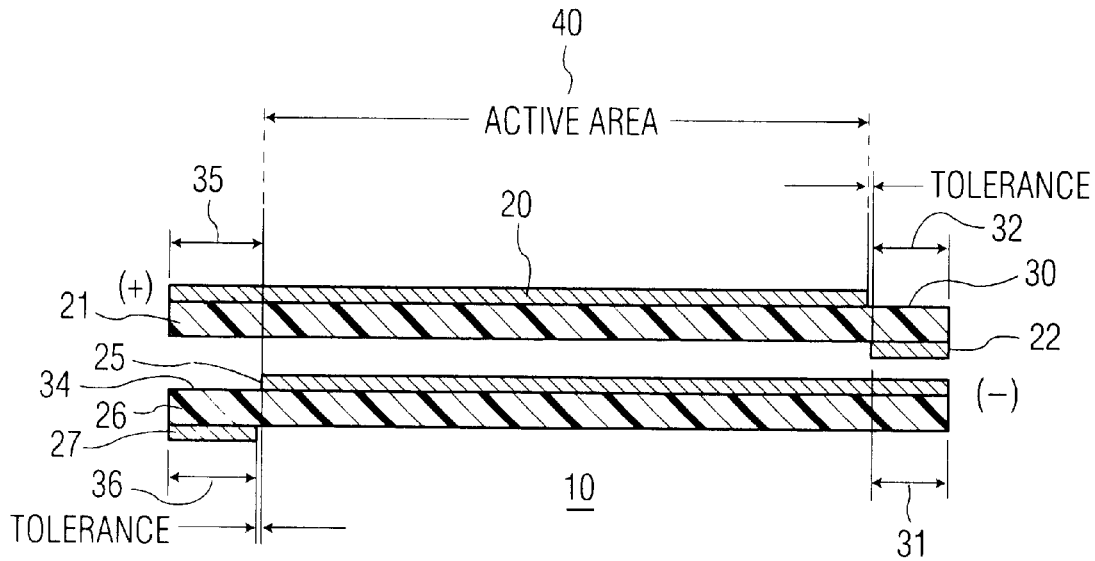
FIG. 2A shows a first exemplary embodiment of a metallized film capacitor employing the present invention.

FIG. 2A shows a wound capacitor 10 comprising a first elongated dielectric web 21 having an electrode 20 metallized on an upper face thereof. A second elongated dielectric web 26 is aligned with and is of the same width as web 21 and also has an electrode 25 metallized on an upper face thereof. Electrodes 20 and 25 are of less width than that of webs 21 and 26 and extend from one longitudinal edge thereof leaving respective safe edges or bare margins 30, 34 of the web along opposite edges thereof. Electrode 20 extends from the left edge of web 21 and electrode 25 extends from the right edge of web 26.

In the exemplary embodiment of the present invention, electrodes 20 and 25 each have a thickness within the range of approximately 5–300 ohms/square. This is strictly exemplary. Thicknesses below 5 ohms/square and above 300 ohms/square are also possible. It should be noted that a more preferred range is from approximately 50–250 ohms/sq. It should further be noted that the most preferred range is from approximately 120–230 ohms/square. Other suitable ranges include greater than 4 ohms/square and greater than 100 ohms/square.

Additionally, in the exemplary embodiment of the present invention, electrodes 20 and 25 are evenly matched in thickness within a specified tolerance. A preferred tolerance for the exemplary embodiment is ±2 ohms/sq. A more preferred tolerance is ±1 ohms/square, and the most preferred tolerance is ±0.5 ohms/sq. For example, if electrode 20 is approximately 42 ohms/square then, most preferably, electrode 25 is between approximately 41.5–42.5 ohms/sq.

In the exemplary embodiment of the present invention, electrodes 22 and 27 each have a thickness of approximately 1–2 ohms/sq. The thickness of electrodes 22 and 27 is greater than the thicknesses of electrodes 20 and 25 because they provide the base onto which the capacitor leads are attached by way of conventional spraying techniques. It is important to note that electrodes 22 and 27 should not extend into the active area 40 of the capacitor. The active area 40 is the portion of the capacitor between respective tolerance regions where a portion of electrode 20 overlaps a portion of electrode 25. If electrodes 22 and/or 27 extend into the active area 40, because they are constructed of relatively heavy metal (e.g., ~2 ohms/$\mu$) rather than thin metal (e.g., ~40 ohms/$\mu$), the improved dielectric strength achieved by reducing the thickness of electrodes 20 and 25 will be adversely affected.

There are several ways for providing the metallization in a metallized capacitor. One way is to use metal foil sheets, although, using current technology, producing foil sheets with the range of thicknesses employed by the present invention may be difficult.

Another way, and the preferred way in manufacturing capacitors employing the present invention, is vapor deposited metal. Vapor deposited metal techniques for standard metallization thickness use a boat for receiving the metal, typically, in wire form. The boat is heated so that a pool of metal is created which is continuously vaporized yet continuously replenished by incoming feed wire. The metal vapor is deposited on a material, typically, the dielectric which continuously passes through the vaporized metal. Standard metallization thicknesses (e.g., 1–4 ohms/square) are achieved using a predetermined speed for feeding the metal wire into the boat as well as a separate predetermined speed for passing the dielectric through the vaporized metal.

One way to achieve the range of thicknesses for the present invention is to adjust the predetermined speeds for the metal wire feed and the passing dielectric. The speeds, which are independently adjustable, should be set to deposit the desired thickness of metallization on the dielectric. For example, this can be accomplished by increasing the speed of the wire feed, increasing the speed of the passing dielectric, or a combination of both.

It should be noted that most types of metals typically used for metallized film capacitors can be employed by the present invention. However, in the exemplary embodiment of the present invention, aluminum is preferred.

It should also be noted that most types of dielectrics typically used for metallized film capacitors can be employed by the present invention. In the exemplary embodiment of the present invention, polyester film is preferred while Mylar is most preferred. Mylar is a trademark of DuPont.

Figure 2B:
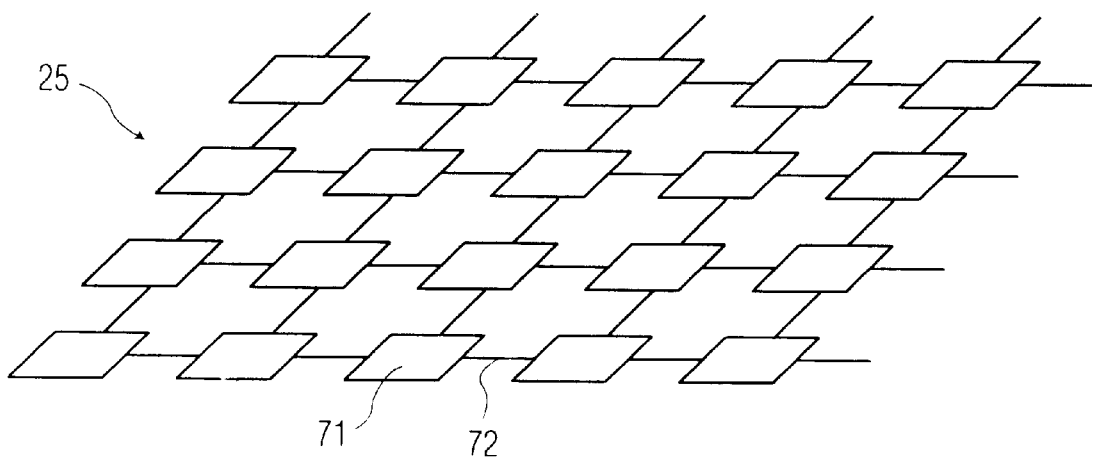
FIG. 2B is a perspective view of at least one of the electrodes shown in FIG. 2A.

As shown in FIG. 2B, electrode 25 is comprised of a plurality of segments 71. Segments 71 are shown in FIG. 1B as having the configuration of squares. Each segment 71, however, can be in other shapes, i.e., rectangles, triangles, irregular, etc. Segments 71 are each connected by wiring 72. These wirings are very thin diameter metallization between the larger segments. Wiring 72 behave as fuses. If an excessive amount of current flows through wiring 72, wiring 72 will break, thus causing electrical isolation between segments on either side of the wiring. This is particularly advantageous in the event of a short.

If substrate 21 develops a pinhole, then a short will develop between electrode 20 and electrode 25. As a result of the short, the capacitor will be damaged as a result of clearings which develop in electrode 20 and electrode 25. As a result of the capacitor being damaged, the life of the capacitor is reduced. Furthermore, the capacitor damage may affect insulation resistance, which in turn affects dissipation factor.

In accordance with the present invention, either electrode 20, or electrode 25, or both, are segmented layers comprising segments 71 interconnected by wiring 72. Segmentation of electrode layers is known as described in Matsui, H., et al., Metalized Film Capacitors with High Energy Density for Rail Vehicles, IEEE Publication 0-7803-4067-1/97, pages 1079 et seq. which is incorporated herein by reference.

If there is a short as a result of pinhole formation in dielectric 21, the amount of current through the wirings which are near the short increases. The excessive current causes the wirings to behave like fuses which blow. The short also causes a clearing to occur in the now electrically isolated segments 71. Thus, the segment with the clearing is isolated from the remainder of the segmented layer within the capacitor.

Electrode 25, with segment 71 and wiring 72, may be formed, for example, using plating technology which is known in the art. The spacing between adjacent segments may be any of several amounts. It is preferred that the spacing between segments be as small as possible so that the amount of metallization per unit-area is as large as possible. The higher the metallization per unit-area, the larger the active area of the capacitor electrode.

Figure 2C:
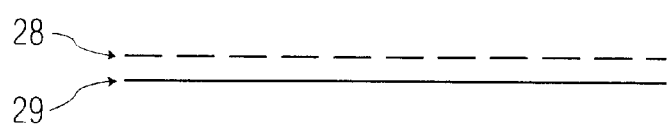
FIG. 2C illustrates a further exemplary embodiment of the present invention.

In an alternative embodiment of the present invention, electrode 20, electrode 25, or both are comprised of more than one layer (see FIG. 2C). Layer 28 is comprised of a segmented layer (as illustrated, for example, in FIG. 2B). Layer 29 is comprised of a continuous layer (without segmentation). Layers 28 and 29 are of sufficient dimension to provide desired dielectric properties to the capacitor. Exemplary dimensions include 2–4 ohms/square for layer 28 and 25–50 ohms/square for layer 29.

Figure 3A:
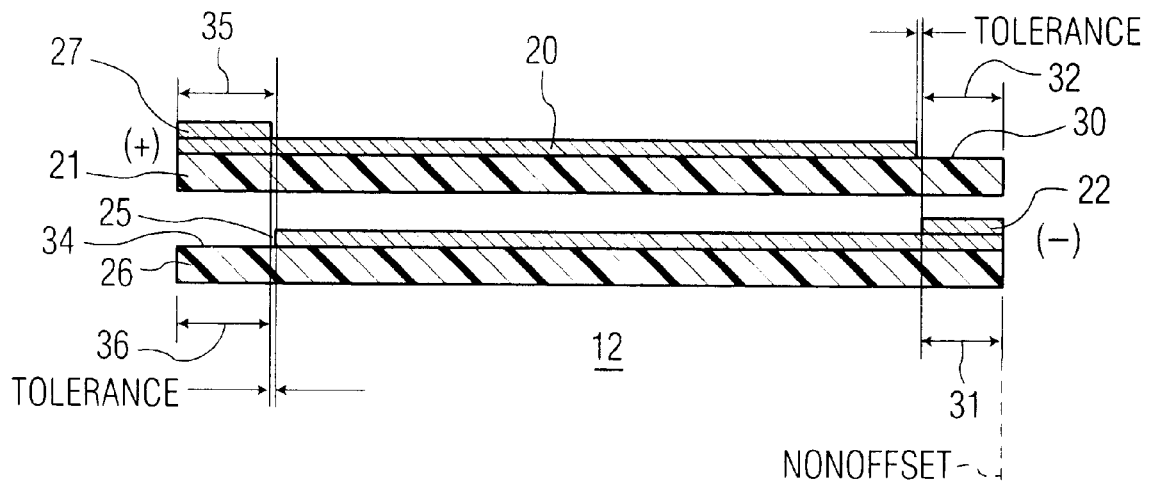
FIG. 3A shows a second exemplary embodiment of a metallized film capacitor employing the present invention.

Referring now to the alternate embodiment of FIG. 3A, a non-offset capacitor 12 is shown comprising a first elongated dielectric web 21 having an electrode 20 metallized on an upper face thereof. A second elongated dielectric web 26 is aligned with and is of the same width as web 21 and also has an electrode 25 metallized on an upper face thereof. Electrodes 20 and 25 are of less width than that of webs 21 and 26 and extend from one longitudinal edge thereof leaving respective safe edges or bare margins 30, 34 of the web along opposite edges thereof. Electrode 20 extends from the left edge of web 21 and electrode 25 extends from the right edge of web 26.

In a preferred embodiment, electrodes 20, 25 are of equal width as are bare margins 30, 34. Margin 30 has a width 32 which together with the width of electrode 20 equals the total width of web 21. Similarly, margin 34 has a width 35 which together with the width of electrode 25 equals the total width of web 26.

As shown in FIG. 3A, the metallized webs 21 and 26 are disposed in superposed relation to each other with the bare margins 30, 34 respectively disposed at opposite edges of the superposed webs.

Electrodes 20 and 25 each include a second portion 27 and 22, respectively, which is relatively thicker than the remainder of the electrode. Second portions 27 and 22, for example, can be 1–4 Ohms/square; whereas, the remainder (or first portions) of electrodes 20 and 25, for example, can be 5–300 Ohms/square. The most suitable thickness for the first portions depends on the thickness (or gauge) of the dielectric. For example, the following table illustrates some breakdown voltages achieved using a first portion thickness with a particular gauge:

TABLE 1

| DIELECTRIC THICKNESS ($\mu$) | FIRST PORTION THICKNESS (Ohms/square) | BREAKDOWN VOLTAGE (Volts) |
| --- | --- | --- |
| 1.58 | 200 | 800 |
| 1.60 | 150 | 780 |

Although Table 1 only presents two examples, as can be appreciated by those skilled in the art, various thicknesses can be employed for various gauges in order to achieve a desired breakdown voltage.

Second portion 22, which is directly below margin 30, extends from the right longitudinal edge of web 21 which is opposite to that edge to which electrode 20 extends. Second portion 22 is of width 31 which is equal to width 32 less a manufacturing tolerance determined by the capabilities of the metallized film converters. Therefore, in the manufacturing process, even if second portion 22 extends to its maximum tolerance width, second portion 22 would not be formed under (opposing relationship with) electrode 20. It will be understood by those skilled in the art that in the manufacturing process that the tolerance may be exceeded in some few cases and second portion 22 may undesirably extend under electrode 20.

Similarly, second portion 27, which is directly above base margins 34, extends from the longitudinal edge (left edge) remote to that edge from which electrode 25 extends. Second portion 27 is of width 36 which is equal to width 35 of margin 34 less the manufacturing tolerance, so that substantially no portion of the area of second portion 27 extends below electrode 25.

It will now be understood that since second portions 22, 27 do not extend below their respective upper electrode layers 20, 25 that there is avoided the requirement for high voltage clearing between the respective upper and lower electrodes. In accordance with the invention as a result of having a greater surface exposed to the metal spray, there is a higher probability of excellent lead termination when the terminals are formed which produces minimum equivalent series resistance (ESR) and minimum dissipation factor. For example, on completion of the winding of the metallized webs into a capacitor roll, relatively thicker second portion provides a thicker surface area for the metal spray. Similarly, on rolling, second portion 27 provides a thicker surface area.

On completion of the winding of capacitor roll 10, the ends may be sprayed with a high velocity mixture of compressed air and molten fine particles of tin produced from an electric arc gun. This spray forms a first terminal (not shown) in contact with second portion 22 and a second terminal in contact with second portion 27. In conventional manner leads may then be respectively bonded to the terminals.

Figure 3B:
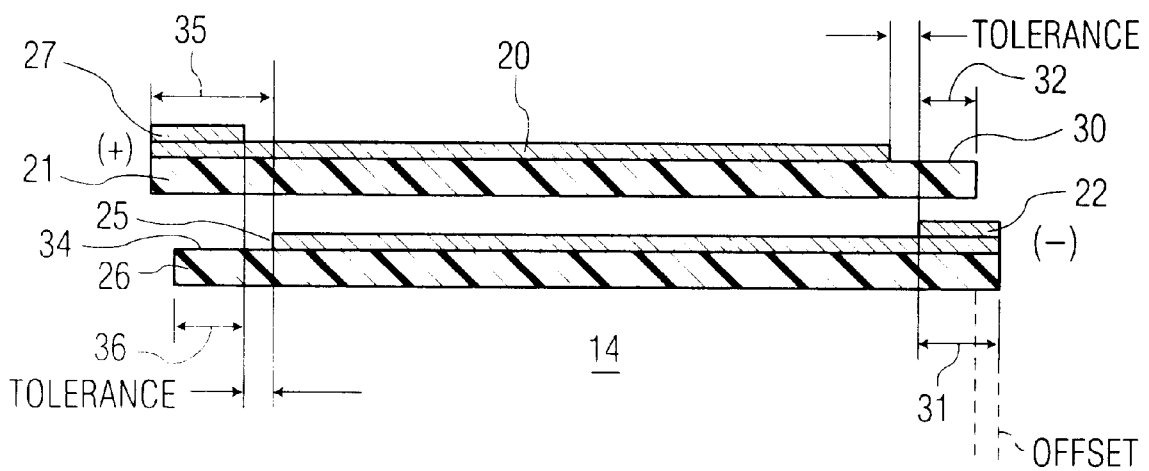
FIG. 3B shows the embodiment of FIG. 3A with an offset.

It will now be understood by those skilled in the art that during the winding process, even though webs 21, 26 are not offset prior to winding and even if there is travel of these webs as a result of machine inconsistencies or film distortion, there will always be on each end of the capacitor exposed metallization. For example, if web 21 wanders to the right with respect to web 26, then second portion 22 is exposed at the right end so that there is a connection between a sprayed terminal and second portion 22 which electrically connects to the rest of electrode 25. It is necessary that the dimension of width 31 be such that the maximum value of such travel is no greater than that dimension. It will further be understood that if the material wander, as shown in FIG. 3B, is such that web 26 wanders to the right with respect to web 21 then electrode 25 is exposed at the right end and is directly in contact with metal spray terminal. It should be noted that an exemplary offset is 0.01 inches.

The above description applies equally to the left end of capacitor 10 in which a wandering of web 26 to the left would expose electrode 27 and a wandering of web 21 to the left would expose electrode 20. Dimension 36 is also related to the maximum travel as above described. Thus, in accordance with the present invention, non-offset wound capacitor 10 provides an increased volumetric efficiency while still permitting sufficient exposed metallization for proper termination even if the film is distorted or the material wanders during winding. It is in this way that the volumetric efficiency is increased by the amount of reduction in offset.

In view of the above, it will now be understood that in a further embodiment of the invention, width 31 of second portion 22 is less than width 32 of the safe edge less the tolerance. Specifically, width 31 of second portion 22 may be only sufficient to meet any irregularities due to the winding machine or film distortion. Thus, even though width 31 is narrower than width 32 (less the tolerance), and web 21 wanders to the right, for example, second portion 22 would still accept a spray terminal, thereby providing an effective capacitor connection. The foregoing also applies to width 36 of second portion 27 being less than margin width 35 (less the tolerance).

Figure 4:
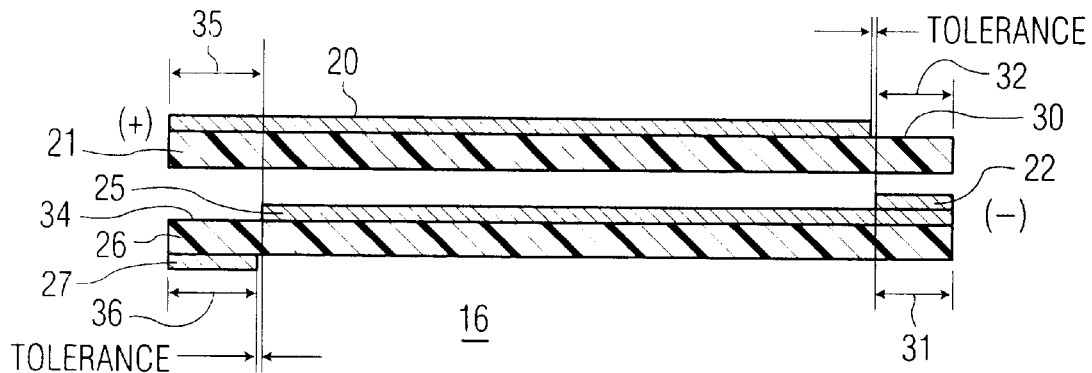
FIG. 4 shows a third exemplary embodiment of a metallized film capacitor employing the present invention.

Another exemplary embodiment is shown in FIG. 4. This embodiment is the same as that described and shown in FIG. 3A except only one of the electrodes (20 or 25) includes a second relatively-thicker portion and the other electrode (25 or 20) is formed in accordance with the techniques taught in U.S. Pat. No. 4,420,097. It should be noted that the side without the relatively-thicker second portion would desirably have a third electrode, as illustrated in FIG. 4, designated with reference numeral 29 and taught in the cited patent.

Figure 5:
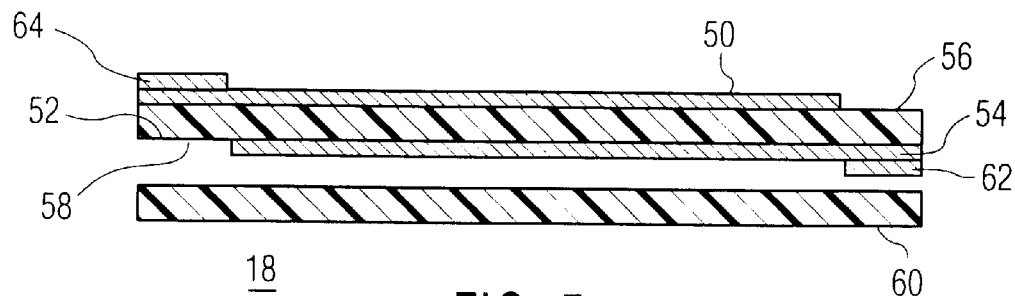
FIG. 5 shows a fourth exemplary embodiment of a metallized film capacitor employing the present invention.

Still another exemplary embodiment, shown in FIG. 5, includes a capacitor 10b which comprises a first elongated dielectric web 52 having an electrode 50 metallized on an upper face thereof. Electrode 50 extends from the left longitudinal edge of web 52 leaving a right safe edge or bare margin 56. A second electrode 54 is metallized on a lower face of web 52 and extends from the right longitudinal edge of web 52 leaving left safe edge or bare margin 58.

In accordance with this further embodiment of the invention, second web 60 is made substantially the same as and is aligned with first web 52. It should be noted that second web 60 is preferably 0.02 inches less than first web 52 in width.

Electrodes 50 and 54 each have relatively thicker second portions 64 and 62, respectively. Second portion 62, which is directly below margin 56, extends from the right longitudinal edge of web 60. Second portion 64, which is directly above margin 58, extends from the left longitudinal edge of web 60. Second portions 62, 64 are preferably about the same width as margins 56, 58 respectively.

Accordingly, in the winding of webs 60, 52, even though webs 52, 60 are of the same width, if there is travel between the webs during the winding process, there is always metallization at the respective end of the capacitor 10b. In this manner, a good electrical connection is provided with as low resistance as possible.

As the thickness of electrode 25 is decreased, dielectric strength is increased and resistivity is increased. Furthermore, as microns per square increases, the resistivity of the roll of which the capacitor is made also increases. As the resistivity increases, the current handling capacity of the capacitor decreases. The inventor believes that by using segments, the micrometers per square can be increased while maintaining dielectric strength.

If electrode 25 was a continuous layer (not segmented), it may be possible to obtain 15 ohms/square as shown in FIG. 1. Such a capacitor may be rated, for example, at 150 volts per micron. For a 2 micron film, for example, 300 volts may be used. By making the metal thinner, a higher resistivity may be obtained and thus more voltage may be obtained. By forming electrode 25 as a plurality of segments, it may be possible to achieve 10 ohms/square at 150 volts per micron.

The greater the thickness of electrode 25, the more damage created during the clearing process. By increasing the metal thickness, however, it may be possible to decrease ohms/square from 15 ohms/square to 10 ohms/square. The fewer ohms/square, the more current the device can handle. The present invention allows the thickness of electrode 25 to be increased and, at the same time, the reliability of the capacitor is increased. If the capacitor develops a fault, which would normally cause the capacitor to break down over a period of time, then the fault would be isolated as a result of the fusing action of the wirings 72.

This is useful for applications such as switching power supplies and high current filter applications.

The size of the wirings (i.e., the fuses) 72 is based upon the desired fusing current. This may be calculated experimentally.

Figure 6:
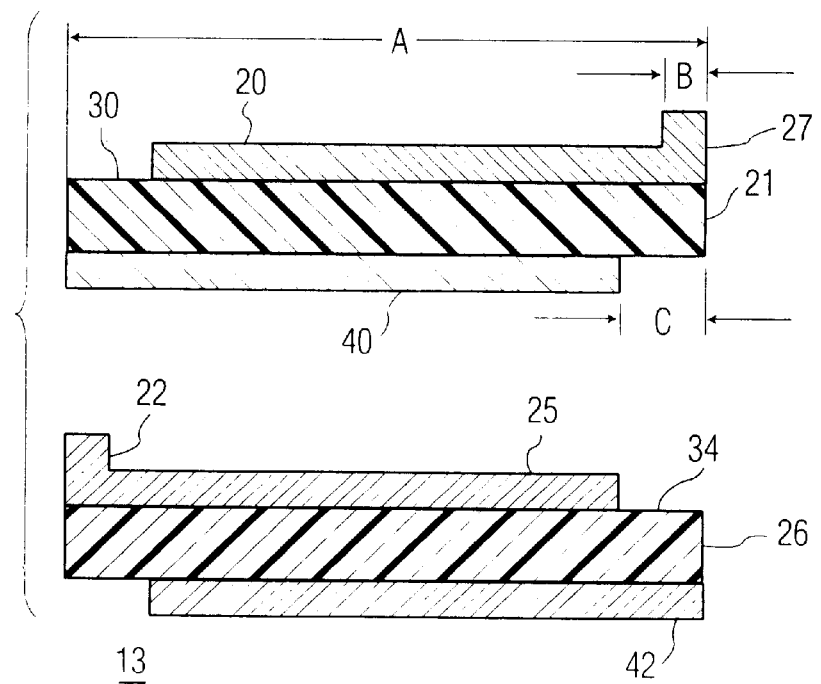
FIG. 6 shows a fifth exemplary embodiment of a metallized film capacitor employing the present invention.

FIG. 6 shows still another alternate embodiment for use with the present invention. This embodiment is similar to that shown in FIG. 3A except that metallization is used on both sides of the dielectrics 21 and 26. The use of the first and second additional layers of metallization 40 and 42 is a solution to a potential problem which can arise when using such thin metallization. The problem is the result of DC corona. If air or gas gets trapped between a layer of metallization (e.g., electrode 25) and the dielectric (e.g., dielectric 21) when winding, it can adversely affect the capacitor.

However, if metallization which extends into the active area is used on both sides of the dielectrics, as shown in FIG. 6, air trapped between two metallizations (e.g., 25 and 40) does not adversely affect the resulting capacitor.

Although the same thin metallization techniques are suitable for use with this embodiment, in the preferred embodiment of FIG. 6, metallization layers 20, 25, 40 and 42 are within the range of 120–230 ohms/square. Again, it is important that the opposing metallization layers are substantially the same thickness.

Also shown in FIG. 6 is the difference in width between width B and width C, thus providing space such that the heavy metal of portions 22 and 27 does not extend into the active region.

Although the present invention has been described with respect to details of contained embodiments thereof, it is not intended that such details be limiting upon the scope of the invention.

What is claimed:

1. A metallized wound capacitor, comprising:

first and second elongated dielectric webs each having a first face, a second face and a width;

a first electrode having first and second portions metallized on the first face of the first web, the first electrode having a width less than the width of the first web;

a second electrode having first and second portions metallized on the first face of the second web, the second electrode having a width less than the width of the second web;

at least one of said first electrode and said second electrode including a plurality of spaced apart segments interconnected by a plurality of wirings;

the first and second electrodes extend from opposing dielectric web longitudinal edges leaving respective bare margins along opposing edges on the respective webs, the second portion of the first electrode opposes the bare margin on the second web and the second portion of the second electrode opposes the bare margin on the first web; and the dielectric webs being arranged in a capacitor roll with the first and second electrodes in superposed relation to each other.

2. A metallized wound capacitor according to claim 1, wherein said first portions of said first and second electrodes being between 5–300 ohms/square.

3. A metallized wound capacitor according to claim 1, wherein each second portion has a width equal to the opposing bare margin less a predetermined tolerance and is thicker than its respective first portion.

4. The metallized wound capacitor of claim 3 in which said first portions of said first and second electrodes are sufficiently thin in order to produce a breakdown voltage of greater than 700 volts.

5. The metallized wound capacitor of claim 1 in which said first portions of said first and second electrodes are between 5–300 Ohms/square.

6. The metallized wound capacitor of claim 1 in which said first portions of said first and second electrodes are between 70–250 Ohms/square.

7. The metallized wound capacitor of claim 1 in which said first portions of said first and second electrodes are between 100–200 Ohms/square.

8. The metallized wound capacitor of claim 1 in which said first portions of said first and second electrodes are substantially 200 Ohms/square for a 1.58 micron dielectric web.

9. The metallized wound capacitor of claim 1 in which said first portions of said first and second electrodes are substantially 150 Ohms/square for a 1.60 micron dielectric web.

10. The metallized wound capacitor of claim 1 in which the webs are offset one from the other prior to being convolutedly arranged in a capacitor roll.

11. The metallized wound capacitor of claim 1 in which there are provided terminals formed by metal spray at the ends of the capacitor roll in contact with the respective first electrode of one web and second electrode of the other web.

12. A metallized wound capacitor, comprising:

first and second elongated dielectric webs each having a first face, a second face and a width;

a first electrode having first and second portions metallized on the first face of the second web, the first electrode having a width less than the width of the first web;

a second electrode having first portion metallized on the first face of the first web, the second electrode having a width less than the width of the second web;

at least one of said first electrode and said second electrode including a plurality of spaced apart segments interconnected by a plurality of wirings;

the first and second electrodes extend from opposing dielectric web longitudinal edges leaving respective bare margins along opposing edges on the respective webs, the second portion of the first electrode opposes the bare margin on the first web;

a third electrode metallized on the second face of the second web; and the dielectric webs being arranged in a capacitor roll with the first and second electrodes in superposed relation to each other.

13. A metallized wound capacitor according to claim 4, wherein said first portions of said first and second electrodes being between 5–300 ohms/square.

14. A metallized wound capacitor according to claim 4, wherein the second portion has a width equal to the opposing bare margin less a predetermined tolerance, the second portion of the first electrode being thicker than its respective first portion.

15. A metallized wound capacitor according to claim 12, wherein the third electrode opposes the bare margin on the first web and has a width equal to the opposing bare margin less a predetermined tolerance.

16. A metallized wound capacitor, comprising:

first and second elongated dielectric webs each having a first face, a second face and a width;

a first electrode having first and second portions metallized on the first face of the first web, the first electrode having a width less than the width of the first web;

a second electrode having first and second portions metallized on the second face of the first web, the second electrode having a width less than the width of the second web;

at least one of said first electrode and said second electrode including a plurality of spaced apart segments interconnected by a plurality of wirings;

the first and second electrodes extend from opposing dielectric web longitudinal edges leaving respective bare margins along opposing edges, the second portion of the first electrode opposes the bare margin on the second face and the second portion of the second electrode opposes the bare margin on the first face; and the dielectric webs being arranged in a capacitor roll with the first and second electrodes in superposed relation to each other.

17. A metallized wound capacitor according to claim 16, wherein each second portion has a width equal to the opposing bare margin less a predetermined tolerance and is thicker than its respective first portion.

18. A method for making a metallized wound capacitor comprising the steps of:

providing first and second elongated dielectric webs each having a first face, a second face and a width;

depositing a first electrode having a plurality of spaced apart segments interconnected by wirings and having first and second portions on the first face of the first web, the first electrode having a width less than the width of the first web;

depositing a second electrode having first and second portions on the first face of the second web, the second electrode having a width less than the width of the second web;

wherein the first and second electrodes extend from opposing dielectric web longitudinal edges leaving respective bare margins along opposing edges on the respective webs, the second portion of the first electrode opposes the bare margin on the second web and the second portion of the second electrode opposes the bare margin on the first web; and arranging the dielectric webs in a capacitor roll with the first and second electrodes in superposed relation to each other.

19. A method for making a metallized wound capacitor according to claim 18 wherein each second portion has a width equal to the opposing bare margin less a predetermined tolerance and is thicker than its respective first portion.

20. A method for making a metallized wound capacitor comprising the steps of:

providing first and second elongated dielectric webs each having a first face, a second face and a width;

depositing a first electrode having first and second portions on the first face of the first web, the first electrode having a width less than the width of the first web;

depositing a second electrode having a plurality of spaced apart segments interconnected by wirings and having first and second portions on the first face of the second web, the second electrode having a width less than the width of the second web;

wherein the first and second electrodes extend from opposing dielectric web longitudinal edges leaving respective bare margins along opposing edges on the respective webs, the second portion of the first electrode opposes the bare margin on the second web and the second portion of the second electrode opposes the bare margin on the first web; and arranging the dielectric webs in a capacitor roll with the first and second electrodes in superposed relation to each other.

21. A method for making a metallized wound capacitor according to claim 20 wherein each second portion has a width equal to the opposing bare margin less a predetermined tolerance and is thicker than its respective first portion.

* * * * *

UNITED STATES PATENT AND TRADEMARK OFFICE
CERTIFICATE OF CORRECTION

PATENT NO. : 6,111,743　　　　　　　　　　　　　　　　　　　　Page 1 of 1
DATED　　　 : August 29, 2000
INVENTOR(S) : Lavene It is certified that error appears in the above-identified patent and that said Letters Patent is hereby corrected as shown below:

Title page, Item [57], ABSTRACT,
Line 6, delete "included" and insert -- comprised --.

Column 10, claim 13,
Line 1, delete "4" and insert -- 12 --.

Column 10, claim 14,
Line 1, delete "4" and insert -- 12 --.

Signed and Sealed this

Thirteenth Day of November, 2001

Attest:

NICHOLAS P. GODICI
Attesting Officer　　Acting Director of the United States Patent and Trademark Office